(12) United States Patent
Ahmed et al.

(10) Patent No.: US 8,288,387 B2
(45) Date of Patent: Oct. 16, 2012

(54) NAPTHALIMIDE-BENZIMIDAZOLE HYBRIDS AS POTENTIAL ANTITUMOR AGENTS AND PROCESS FOR THE PREPARATION THEREOF

(75) Inventors: Kamal Ahmed, Andhra Pradesh (IN); Praveen Kumar Pogula, Andhra Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 12/920,911

(22) PCT Filed: Mar. 3, 2009

(86) PCT No.: PCT/IN2009/000141
§ 371 (c)(1),
(2), (4) Date: Mar. 22, 2011

(87) PCT Pub. No.: WO2009/110000
PCT Pub. Date: Sep. 11, 2009

(65) Prior Publication Data
US 2011/0166346 A1  Jul. 7, 2011

(30) Foreign Application Priority Data
Mar. 5, 2008 (IN) .............................. 517/DEL/2008

(51) Int. Cl.
C07D 401/12 (2006.01)
C07D 401/14 (2006.01)
C07D 403/02 (2006.01)
C07D 403/14 (2006.01)
A61K 31/4523 (2006.01)
A61K 31/4353 (2006.01)

(52) U.S. Cl. ................... 514/253.03; 514/296; 544/361; 546/110

(58) Field of Classification Search ........................ None
See application file for complete search history.

(56) References Cited

U.S. PATENT DOCUMENTS
6,300,331 B1 * 10/2001 Noguchi et al. ......... 514/253.03

OTHER PUBLICATIONS
Hörig et al., J. Translational Med. 2:44 (2004).*

* cited by examiner

Primary Examiner — Joseph K. McKane
Assistant Examiner — Michael Barker
(74) Attorney, Agent, or Firm — Ladas & Parry LLP

(57) ABSTRACT

The present invention provides the compounds of general formula 5 and 9 useful as potential antitumour agents against human cancer cell lines. The present invention further provides the process for preparation of napthalimide-benzimidazole hybrids of general formula 5 and 9, n-1-2, R=n-methylpiperazine or morpholine (Formula 9), wherein: n=2-3, m=2-3 and R=n-methylpiperazine or morpholine.

Formula 5

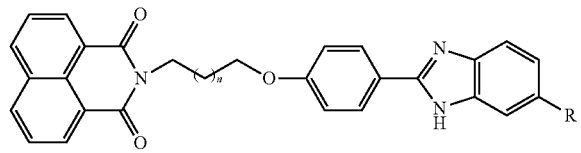

Formula 9

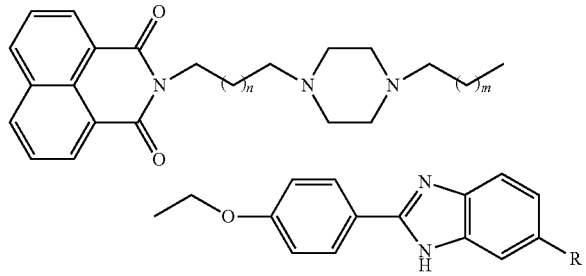

14 Claims, No Drawings

NAPTHALIMIDE-BENZIMIDAZOLE HYBRIDS AS POTENTIAL ANTITUMOR AGENTS AND PROCESS FOR THE PREPARATION THEREOF

FIELD OF THE INVENTION

The present invention relates to novel napthalimide-benzimidazole hybrids as potential antitumour agents and process for the preparation thereof. More particularly, it provides process for the preparation of 2-{3-[4-(6-[4-methylpiperazino]2-benzimidazolyl)phenoxy]propyl}napthalimide/2-{4-[4-(6-morpholino-2-benzimidazolyl)phenoxy]butyl}napthalimide/2-{4-[4-(4-[4-(6-[4-methylpiperazino]2-benzimidazolyl)phenoxy]butyl)piperazino]butyl}napthalimide/2-{5-[4-(5-[4-(6-morpholino-2-benzimidazolyl)phenoxy]pentyl)piperazino]pentyl}napthalimid with aliphatic chain length variations. and thereby antitumour activity. The structural formula of these napthalimide-benzimidazole hybrids is given below.

Formula A

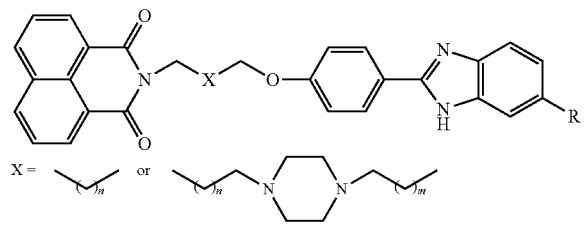

Wherein R is n-methylpiperazine or morpholine; n=1-3, m=2-3

The napthalimide-benzimidazole hybrid of formula A is further represented by the compounds of formula 5 and 9 as herein, given below:

Formula 5

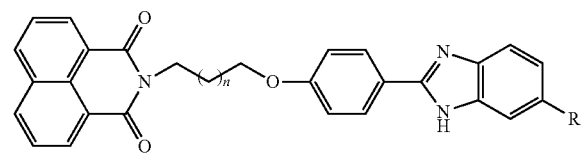

wherein: n=1-2, R=n-methylpiperazine or morpholine

Formula 9

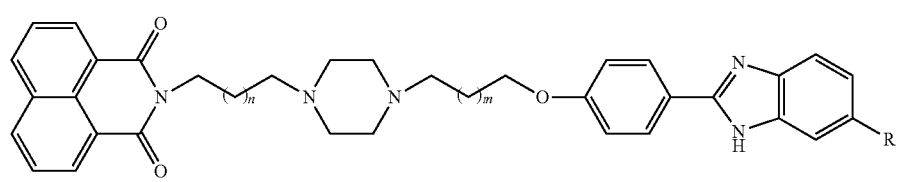

wherein: n=2-3, m=2-3 and R=n-methylpiperazine or morpholine

BACKGROUND OF THE INVENTION

The benzimidazoles are potent antitumour, antifungal and antiparasitic agents, whose mode of action is thought to result from their inhibition of microtubule formations (Goker, H.; Kus, C.; Boykin, D. W.; Yildiz, S.; Altanlar, N. *Bioorg. Med. Chem.* 2002, 10, 2859.; Seth, P. P.; Jefferson, E. A.; Risen, L. M.; Osgood, S. A. *Bioorg. Med. Chem. Lett.* 2003, 13, 1669.; Nare, B.; Liu, Z.; Prichard, R. K.; George, E. *Biochem. Pharmacol.* 1994, 48, 2215). Substituted benzimidazoles have proven as drug leads, which have exhibited pharmacological interest. A series of 2-phenyl benzimidazole-4-carboxamides have been synthesized and evaluated for in vitro and in vivo antitumour activity (Mahaimeed, H. A. *Int. Med. Res.* 1997, 25, 175.; Denny, W. A.; Rewcastle, G. W.; Baguly, B. C. *J. Med. Chem.* 1990, 33, 814). One of the bisbenzimidazole (Hoechst-33258) is known for the inhibition of DNA topoisomerase I with affinity to AT-rich sequences in DNA (Chen, A. Y.; Yu, C.; Bodley, A.; Peng, L. F.; Liu, L. F. *Cancer Res.* 1993, 53, 1332.; Alper, S.; Arpaci, O. T. E. S.; Aid, E.; Yalc, I. *II Farmaco* 2003, 58, 497.; Czarny, A.; Boykin, D. W.; Wood, A. A.; Nunn, C. M.; Neidle, S.; Zhao, M.; Wilson, W. D. *J. Am. Chem. Soc.* 1995, 117, 4716; Embrey, K. J.; Searle, M. S.; Craik, D. J. *J. Chem. Soc. Chem. Commun.* 1991, 1770; Fede, A.; Billeter, M.; Leupin, W.; Thrich, K. W. *Structure* 1993, 1, 177; 42.; Haq, I.; Ladbury, J. E.; Chowdhry, B. Z.; Jenkins, T. C.; Chaires, J. B. *J. Mol. Biol.* 1997, 271, 244). Based on such interesting results, a variety of bisbenzimidazole derivatives have been designed and synthesized. This addition of a benzimidazole unit in these dimers significantly enhanced the interaction with DNA to raise the ΔTm value to more than 20° C. Further the DNA footprinting experiments have shown that five to six base pairs are protected by trisbenzimidazole derivatives and possess potential of this class of compounds for the development of anticancer agents with DNA sequence recognition (Hua, J. Y.; Bur, D.; Hasler, W.; Schmitt, V. R.; Dorn, A.; Bailly, C.; Waring, M. J.; Hochstrassera, R.; Leupina, W. *Bioorg. Med. Chem.* 2001, 9, 2905).

Napthalimides are another interesting pharmacophores in the design of mono as well as bisintercalaters with good antitumour activity, some of these compounds like amonafide and mitonafide bind to double stranded DNA by intercalation and underwent clinical studies (Brana, M. F.; Ramos, A. *Curr. Med. Chem. Anticancer Agents* 2001, 1, 237.; Malviya, P. V. K.; Liu, Y.; Alberts, D. S.; Surwit, E. A.; Craig, J. B.; Hanningan, E. V. *Am. J. Clin. Oncol.* 1992, 15, 41.; Bousquet, P. F.; Brana, M. F.; Conlon, D.; Fitzgerald, K. M.; Perron, D.; Cocchiaro, C.; Miller, R.; Moran, M.; George, J.; Qian, X. D.; Keilhauer, G.; Romerdahl, C. *Cancer Res.* 1995, 55, 1176). Bisintercalation obtained by dimerization of these napthalimides exhibit much higher activity than the monomeric compounds and one such example is elinafide, which shows potent cellular cytotoxicity with excellent in vivo antitumour activity (Bailly, C.; Brana, M. F.; Waring, M. J. *Eur. J. Biochem.* 1996, 240, 195.; Brana, M. F.; Castellano, J. M.; Mora, M.; Vega, M. J. P; Romerdahl, C. R.; Qian, X. D.; Bousquet, P.; Emling, F.; Schlick, E.; Keilhauer, G. *Anticancer Drug Des.* 1993, 8, 257.; Brana, M. F.; Castellano, J. M.; Mora, M.; Vega, M. J. P; Perron, D.; Conlon, D.; Bousquet, P. F.; Romerdahl, C. A.; Robinson, S. P. *Anticancer Drug Des.* 1996, 11, 297; Thompson, J.; Pratt, C. B.; Stewart, C. F.; Bowman, L.; Zamboni, W. C.; Pappo, A. *InVest. New Drugs* 1998, 16, 45). Detailed molecular biology experiments have indicated that these bisnapthalimides intercalate DNA helix through the major groove (Bailly, C.; Brana, M. F.; Waring, J. *Eur. J. Biochem.* 1996, 240, 1955; (b) Gallego, J.; Reid, B. R. *Biochemistry* 1999, 38, 15104) and hence such a pharmacophore is important in the design of new chemical entities with anticancer activity.

This is in continuation to our earlier efforts towards the synthesis of new class of pyrrolobenzodiazepine (PBD) hybrids, which have the ability to recognize and subsequently form covalent bonds to specific base sequences of double stranded DNA (Thurston, D. E. In *Molecular Aspects of Anticancer Drug—DNA Interactions.*; Neidle, S.; Waring, M. J.; Eds.; Macmillan. London 1993, 1, 54.; Thurston, D. E. Br. J. *Cancer* 1999, 80, 65.; Thurston, D. E.; Morris, S. J.; Hartley, J. A. *Chem. Commun.* 1996, 563; Wilson, S. C.; Howard, P. W.; Forrow, S. M.; Hartley, J. A.; Adams, L. J.; Jenkins, T. C.; Kelland, L. R.; Thurston, D. E. *J. Med. Chem.* 1999, 42, 4028), we have recently prepared PBD-napthalimide and PBD-benzimidazole conjugates. These have exhibited DNA binding ability and remarkable anticancer activity (Kamal, A.; Reddy, B. S. N.; Reddy, G. S. K.; Ramesh, G. *Bioorg. Med. Chem. Lett.* 2002, 12, 1933.; Kamal, A.; Srinivas, O.; Ramulu, P.; Kumar, P, P. *Bioorg. Med. Chem. Lett.* 2003, 13, 3577.; Kamal, A.; Ramulu, P.; Srinivas, O.; Ramesh, G.; Kumar, P. P. *Bioorg. Med. Chem. Lett.* 2004, 12, 4337). This concept of mixed hybrids for dual action has been further taken forward in the present study wherein napthalimide moiety has been linked to the benzimidazole scaffold by suitable linker spacers. In this investigation two type of linker spacers have been utilized, that is one without piperazine moiety while the other with a piperazine moiety to improve the lipophilicity and also to understand the structure activity relationship aspects.

OBJECTIVES OF THE INVENTION

The main objective of the present invention is to provide novel napthalimide-benzimidazole hybrids useful as antitumour agents.

Yet another object of the present invention is to provide a process for the preparation of novel napthalimide-benzimidazole hybrids.

SUMMARY OF THE INVENTION

Accordingly the present invention provides novel napthalimide-benzimidazole hybrids of formula A useful as potential antitumour agents

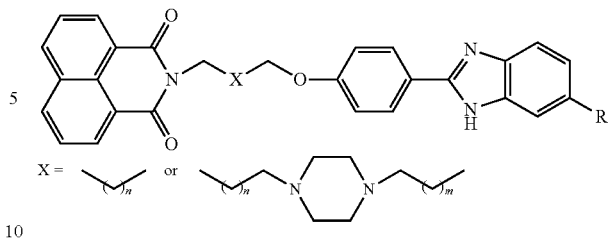

wherein R is n-methylpiperazine or morpholine; n=1-3; m=2-3.

In an embodiment of the present invention the novel napthalimide-benzimidazole hybrid of formula A is represented by the compounds of formula 5 and 9

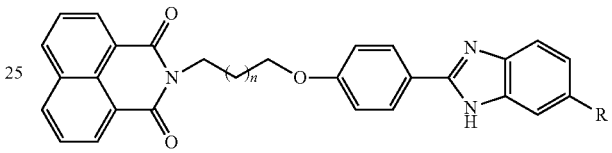

Formula 5 wherein 'n' is 1-2; R=morpholine or n-methylpiperazine

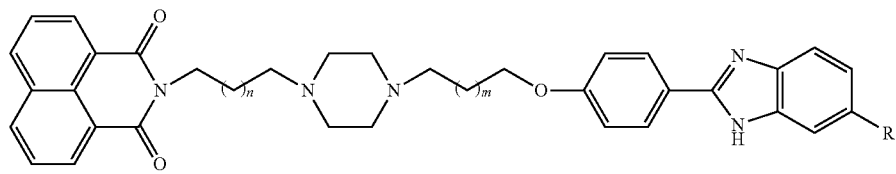

Formula 9 wherein 'n' is 2-3; m is 2-3; R=morpholine or n-methylpiperazine

In yet another embodiment the representative compounds of formula A are:

2-{3-[4-(6-[4-methylpiperazino]2-benzimidazolyl)phenoxy]propyl}napthalimide (5a), 2-{4-[4-(6-morpholino-2-benzimidazolyl)phenoxy]butyl}naphthalimide (5b), 2-{4-[4-(4-[4-(6-[4-methylpiperazino]-2-benzimidazolyl)phenoxy]butyl)piperazino]butyl}napthalimide (9a), 2-{4-[4-(4-[4-(6-morpholino-2-benzimidazolyl)phenoxy]butyl)piperazino]butyl}napthalimide (9b), 2-{5-[4-(5-[4-(6-morpholino-2-benzimidazolyl)phenoxy]pentyl)piperazino]pentyl}napthalimide (9c), In yet another embodiment the general structure of the representative compounds of formula A are:

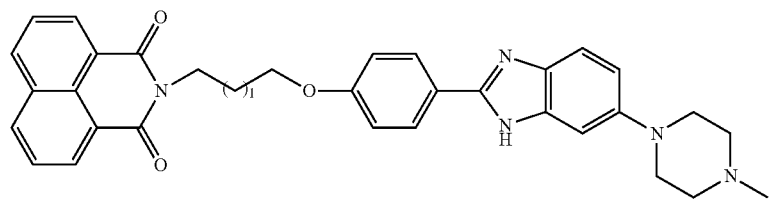
5a
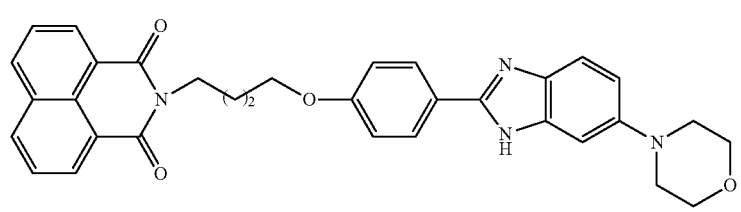
5b
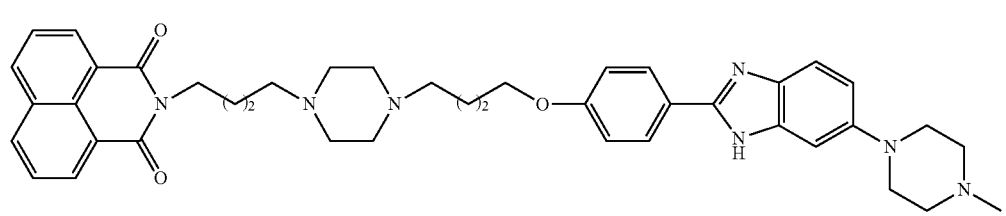
9a
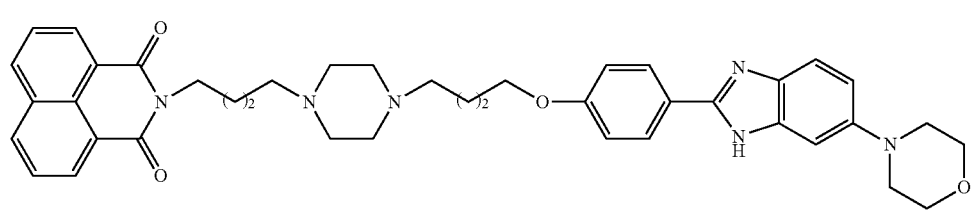
9b
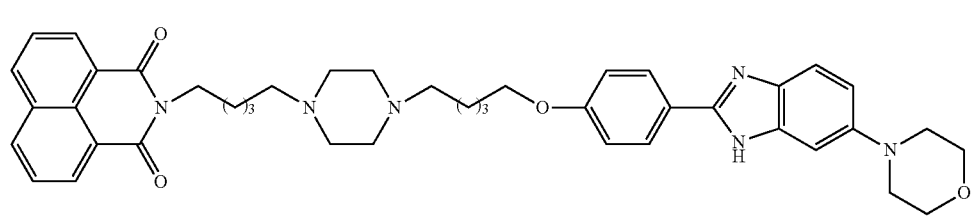
9c

The present invention further provides a process for the preparation of novel napthalimide-benzimidazole hybrids of formula A comprising 5a-b and 9a-c and the said process comprising the steps of
   a) reacting 1,8-napthalimide with dibromoalkanes, in the presence of potassium carbonate in DMF and the isolating the compounds 2-(n-bromoalkyl)napthalimide of formula 3a-c,
   b) reacting the above said bromo compounds of formula 3a-b with 4-hydroxybenzaldehyde in presence of dimethylformamide and $K_2CO_3$, at a temperature of 25-30° C., for a period of 20-30 hrs and isolating the compound 4-[n-(napthalimide-2-yl)alkoxy]benzaldehyde of formula 4a-b,
   c) condensing and oxidizing the above said aldehyde compounds of formula 4a-b with diaminobenzene derivatives of formula 4-(4-methylpiperazino)-1,2-benzenediamine or 4 morpholino-1,2-diaminobenzene, in the presence of $Na_2S_2O_5$ and organic solvent selected from methanol and ethanol, under refluxing temperature and isolating the desired compounds of 2-{3-[4-(6-[4-Methylpiperazino]2-benzimidazolyl)phenoxy]propyl}napthalimide or 2{4-[4-(6-Morpholino-2-benzimidazolyl)phenoxy]buty-1}napthalimide of formula 5a-b.
   d) reacting 2-(n-bromoalkyl)napthalimide of formula 3a-c with n-Bocpiperazine, in the presence of potassium carbonate in DMF and isolating tert-Butyl4-[n-(2-napthalimido)alkyl]-1-piperazinecarboxylate of formula 6a-b,
   e) deprotection the above said Boc compounds of formula 6a-b using trifluoro acetic acid, in the presence of dichloromethane at about 0° C., for a period of 10-20 hrs and isolating the compound 4-[n-(2-napthalimido)alkyl]-1-piperazine of formula 7a-b,
   f) reacting the above said free amine compounds of formula 7a-b with bromo alkoxy benzaldehydes, in the presence of acetonitrile/$K_2CO_3$, at refluxing temperature, for a period of 20-25 hrs and isolating the compound of 4-{n-[4-(n-[2-Napthalimido]alkyl)piperazino]alkoxy}benzaldehyde of formula 8a-b,
   g) condensing and oxidizing the above said aldehyde compounds of formula 8a-b with diaminobenzene derivatives of formula 2a-b $Na_2S_2O_5$ and organic solvent selected from methanol and ethanol, under refluxing temperature and isolating the desired compounds of novel napthalimide-benzimidazole hybrids of formula 9a-c.

In still another embodiment the novel napthalimide-benzimidazole hybrids of formula 5 and 9 obtained exhibit an in vitro anticancer/antitumour activity against sixty human cancer cell lines derived from nine cancer types selected from the group consisting of leukemia, non-small-cell lung, colon, CNS, melanoma, ovarian, prostate, and breast cancer.

DETAILED DESCRIPTION OF THE INVENTION

The precursors 4-[3-(napthalimide-2-yl)propoxy]benzaldehyde/4-[4-(napthalimide-2-yl)butoxy]benzaldehyden of formula 4a-b and 4-{4-[4-(4-[2-napthalimido]butyl)piperazino]butoxy}benzaldehyde/4-{5-[4-(5-[2-napthalimido]pentyl)piperazino]pentoxy}benzaldehyde of formula 8a-b (Kamal, A.; Reddy, B. S. N.; Reddy, G. S. K.; Ramesh, G. Bioorg. Med. Chem. Lett. 2002, 12, 1933; Kamal, A.; Srinivas, O.; Ramulu, P.; Kumar, P, P. Bioorg. Med. Chem. Lett. 2003, 13, 3577) have been prepared by literature methods. The diamine precursors 2a-b have been prepared by the treatment of 5-chloro-2-nitroaniline with n-methylpiperazine or morpholine in the presence of potassium carbonate to give nitro compound of formula 1a-b, followed by reduction using Pd/C provides formula 2a-b (Hua, J. Y.; Bur, D.; Hasler, W.; Schmitt, V. R.; Dorn, A.; Bailly, C.; Waring, M. J.; Hochstrassera, R.; Leupina, W. Bioorg. Med. Chem. 2001, 9, 2905). Novel napthalimide-benzimidazole conjugates of formula 5a-b and 9a-c have been carried out by condensation of the substituted diamines of formula 2a-b with different aldehydes of formula 4a-b or 8a-c (Bathini, Y.; Lown, J. W. Synthetic Commun. 1990, 20, 955).

Some representative compounds of formula 5 and 9 for the present inventions are given below
a) 2-{3-[4-(6-[4-methylpiperazino]2-benzimidazolyl)phenoxy]propyl}napthalimide
b) 2-{4-[4-(6-morpholino-2-benzimidazolyl)phenoxy]butyl}naphthalimide
c) 2-{4-[4-(4-[4-(6-[4-methylpiperazino]-2-benzimidazolyl)phenoxy]butyl)piperazino]butyl}napthalimide
d) 2-{4-[4-(4-[4-(6-morpholino-2-benzimidazolyl)phenoxy]butyl)piperazino]butyl}napthalimide
e) 2-{5-[4-(5-[4-(6-morpholino-2-benzimidazolyl)phenoxy]pentyl)piperazino]pentyl}napthalimide These new analogues of naphthalimide-benzimidazole hybrids have shown remarkable anticancer activity in various cell lines. This present invention is illustrated in Scheme 1 and Scheme 2 which comprise:
   1) Oxidation of diamine intermediates with aldehyde moieties.
   2) Refluxing the reaction mixtures for 8 h.
   3) Synthesis of napthalimide-benzimidazole antitumour antibiotic hybrids.
   4) Purification by column chromatography using different solvents like ethyl acetate, hexane, chloroform and methanol.

Representative compounds 5a-b and 9a-c of general structural formula 5 and 9

| Compound | R                  | n | m |
|----------|--------------------|---|---|
| 5a       | n-methylpiperazine | 1 | — |
| 5b       | morpholine         | 2 | — |
| 9a       | n-methylpiperazine | 2 | 2 |
| 9b       | morpholine         | 2 | 2 |
| 9c       | morpholine         | 3 | 3 |

Scheme 1

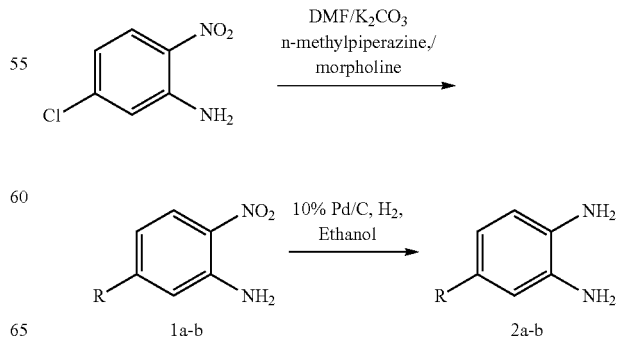

Scheme 2
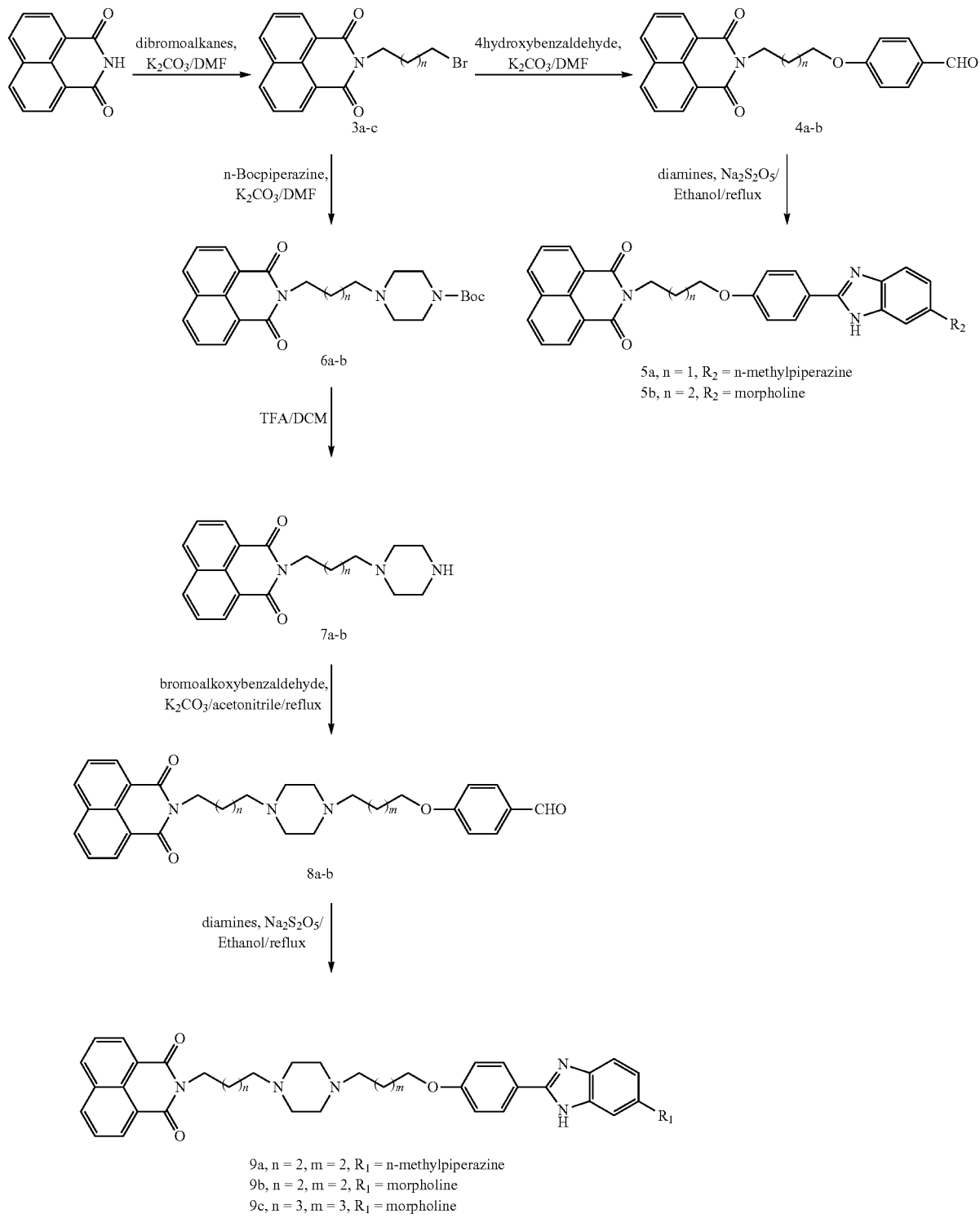
5a, n = 1, R$_2$ = n-methylpiperazine
5b, n = 2, R$_2$ = morpholine
9a, n = 2, m = 2, R$_1$ = n-methylpiperazine
9b, n = 2, m = 2, R$_1$ = morpholine
9c, n = 3, m = 3, R$_1$ = morpholine
3a, n = 1, 3b, n = 2, 3c, n = 3;
4a, n = 1, 4b, n = 2;
6a, n = 2, 6b, n = 3;
7a, n = 2, 7b, n = 3;
8a, n = 2, m = 2, 8b, n = 3, m = 3

The following examples are given by way of illustration of the working of the invention in actual practice and therefore should not be construed to limit the scope of present invention in any way.

EXAMPLE 1

To a solution of 1,8-napthalimide (198 mg, 1 mmol) in dry DMF (7 mL) was added anhydrous $K_2CO_3$ (552 mg, 4 mmol) and the 1,3-dibromopropane (808 mg, 4 mmol). The reaction mixture was stirred at room temperature for 24 h. The reaction was monitored by TLC using EtOAc/hexane (2:8) as a solvent system, and then extracted with ethyl acetate and cool water (3×30 mL). The organic phase was dried over $Na_2SO_4$ and evaporated under vacuum to afford the crude product was purified by column chromatography using 10% EtOAc-Hexane as eluent to afford pure compound of white solid 3a (270 mg, 85%).

$^1$H NMR (200 MHz, $CDCl_3$): δ8.5 (d, 2H), 8.16-8.19 (dd, J=8.3, 1.5 Hz, 2H), 7.73 (t, J=7.5 Hz, 2H), 4.28 (t, J=6.7 Hz, 2H), 3.47 (t, J=6.79, 2H), 2.25-2.35 (q, 2H)

MS (EI) 318 [M]$^+$.

To compound 2-(3-bromopropyl)napthalimide 3a (318 mg, 1 mmol) in dry DMF (7 mL) was added anhydrous $K_2CO_3$ (552 mg, 4 mmol) and the 4-Hydroxybenzaldehyde (122 mg, 1 mmol). The reaction mixture was stirred at room temperature for 24 h, until TLC indicates complete loss of starting material. The potassium carbonate was removed by suction filtration and the solvent was removed under vacuum. The crude product was purified by column chromatography using 60% EtOAc-hexane as eluent to afford pure compound of white solid 4a (269 mg, 75%).

$^1$H NMR (300 MHz, $CDCl_3$): δ 9.83 (S, 1H), 8.57 (d, 2H), 8.17 (d, J=8.30 Hz, 2H), 7.70-7.76 (t, J=7.55, 2H), 7.31 (d, J=4.5, 2H), 6.95 (d, J=8.3 Hz, 2H), 4.25-4.32 (t, 6.79, 2H), 3.44-3.51 (t, J=6.79, 2H), 2.25-2.35 (q, 2H)

MS (EI) 359 [M]$^+$.

To a solution of 5-cholro-2-nitroaniline (172 mg, 1 mmol), n-methylpiperazine (100 mg, 1 mmol) and potassium carbonate (552 mg, 4 mmol) in DMF (5 mL) was heated at 100° C. for 6 h and then cooled to room temperature. After addition of 20 mL of water, the resulting precipitate was filtered and the obtained solid was suspended in 25 mL of 2N acetic acid and filtered. The filtrate was slightly basified with ammonia solution and the resulting precipitate was filtered off to give the compound 1a (188 mg, 80%) as a yellow solid.

$^1$H NMR ($CDCl_3$): δ 2.39 (s, 3H), 2.40-2.50 (m, 4H), 3.28-3.48 (m, 4H), 6 11 (d, 1H, J=8.8 Hz), 6.15-6.23 (dd, 1H, J=8.4 Hz, 1.9 Hz), 6.85 (bs, 2H), 7.92 (d, 1H, J=8.4 Hz).

MS (EI) 236 [M]$^+$.

To compound 1a (377 mg, 1.6 mmol) in ethanol (10 mL) was hydrogenated over 10% Pd/C (50 mg) at room temperature for 3 h. After hydrogenation, 4-[3-(napthalimide-2-yl)propoxy]benzaldehyde 4a (359 mg, 1 mmol) and 3 mL of aqueous solution of sodium pyrosulphate (270 mg, 1.5 mmol) in water were added. The reaction mixture was stirred at reflux for 12 h and then cooled to room temperature. The reaction was monitored by TLC using MeOH/EtOAc (2:8) as a solvent system, and then extracted with ethyl acetate. The organic phase was dried over $Na_2SO_4$ and evaporated under vacuum to afford the crude product was purified by column chromatography using 5% MeOH—$CHCl_3$ as eluent to afford pure compound 5a (327, 60%).

$^1$H NMR (300 MHz $CDCl_3$): δ 8.60 (d, J=7.2 Hz, 2H), 8.25 (d, J=7.9 Hz, 2H), 7.83 (d, J=8.5 Hz, 2H), 7.73 (t, J=7.9 Hz, 2H), 7.47 (d, J=8.7 Hz, 1H), 6.90-7.10 (m, 2H), 6.85 (d, J=7.0 Hz, 2H), 4.40 (t, 2H, J=5.3 Hz), 4.15 (t, J=6.1 Hz, 2H), 3.65-3.75 (m, 4H), 2.65-2.75 (m, 4H), 2.4 (S, 3H), 2.20-2.35 (m, 2H).

ESI M S m/z=546 (M+1)$^+$.

EXAMPLE 2

To a solution of 1,8-napthalimide (198 mg, 1 mmol) in dry DMF (7 mL) was added anhydrous $K_2CO_3$ (552 mg, 4 mmol) and the 1,4-dibromobutane (860 mg, 4 mmol). The reaction mixture was stirred at room temperature for 24 h, until the reaction was monitored by TLC using EtOAc/hexane (2:8) as a solvent system, and then extracted with ethyl acetate and cool water (3×30 mL). The organic phase was dried over $Na_2SO_4$ and evaporated under vacuum to afford the crude product was purified by column chromatography using 10% EtOAc-Hexane as eluent to afford pure compound of white solid 3b (282 mg, 85%)

$^1$H NMR (200 MHz, $CDCl_3$): δ 8.56 (d, 2H), 8.15-8.17 (dd, J=8.30, 1.51 Hz, 2H) 7.74 (t, J=7.5 Hz, 2H) 4.25 (t, 6.79, 2H), 3.45 (t, J=6.7 Hz, 2H), 2.20-2.30 (m, 4H)

MS (EI) 332 [M]$^+$.

To compound 2-(4-bromobutyl)napthalimide 3b (332 mg, 1 mmol) in dry DMF (8 mL) was added anhydrous $K_2CO_3$ (552 mg, 4 mmol) and the 4-Hydroxybenzaldehyde (122 mg, 1 mmol). The reaction mixture was stirred at room temperature for 24 h, until TLC indicates complete loss of starting material. The potassium carbonate was removed by suction filtration and the solvent was removed under vacuum. The crude product was purified by column chromatography using 70% EtOAc-hexane as eluent to afford pure compound of white solide 4b (290 mg, 78%).

$^1$H NMR (300 MHz, $CDCl_3$): δ 9.83 (S, 1H), 8.57 (d, 2H), 8.16-8.19 (d, J=8.30 Hz, 2H), 7.70-7.76 (t, J=7.55, 2H), 7.31 (d, J=4.5, 2H), 6.95 (d, J=8.3 Hz, 2H), 4.25-4.32 (t, 6.79, 2H), 3.44-3.51 (t, J=6.79, 2H), 2.25-2.35 (q, 2H)

MS (EI) 373 [M]$^+$.

To a solution of 5-cholro-2-nitroaniline (172 mg, 1 mmol), morpholine (87 mg, 1 mmol) and potassium carbonate (138 mg, 1 mmol) in DMF (5 mL) was heated at reflux for 3 h and then cooled to room temperature. After addition of 20 mL of water, the resulting precipitate was filtered and the obtained solid was suspended in 25 mL of 2N acetic acid and filtered. The filtrate was slightly basified with ammonia solution, and the resulting precipitate was filtered off to give the compound 1b (167 mg, 75%) as a yellow solid.

$^1$H NMR (200 MHz $CDCl_3$): δ 2.39 (s, 3H), 2.40-2.50 (m, 4H), 3.28-3.48 (m, 4H), 6 10 (d, 1H, J=8.8 Hz), 6.15-6.23 (dd, J=8.4 Hz, 1.9 Hz, 1H), 6.85 (bs, 2H), 7.9 (d, J=8.4 Hz, 1H)

MS (EI) 223 [M]$^+$.

To 1b (356 mg, 1.6 mmol) in ethanol (10 mL) was hydrogenated over 10% Pd/C (50 mg) at room temperature for 2 h. After hydrogenation, 4-[4-(napthalimide-2-yl)butoxy]benzaldehyde 4b (373 mg, 1 mmol) and 3 mL of aqueous solution of sodium pyrosulphate (275 mg, 1.5 mmol) in water were added. The reaction mixture was stirred at reflux for 12 h and then cooled to room temperature. The reaction was monitored by TLC using MeOH/EtOAc (2:8) as a solvent system, and then extracted with ethyl acetate. The organic phase was dried over $Na_2SO_4$ and evaporated under vacuum to afford the crude product was purified by column chromatography using 4% MeOH—$CHCl_3$ as eluent to afford pure compound 5b (311 mg, 57%)

$^1$H NMR (300 MHz $CDCl_3$): δ 8.61 (d, J=7.2 Hz, 2H), 8.24 (d, J=7.9 Hz, 2H), 7.88 (d, J=8.5 Hz, 2H), 7.77 (t, J=7.9 Hz, 2H), 7.48-7 (d, J=8.7 Hz, 1H), 6.90-7.10 (m, 2H), 6.86 (d,

J=7.0 Hz, 2H), 4.42 (t, J=5.3 Hz, 2H), 4.17 (t, J=6.1 Hz, 2H), 3.65-3.75 (m, 4H), 2.65-2.75 (m, 4H), 2.4 (S, 3H), 2.20-2.35 (m, 2H).

ESI M S m/z=547 (M+1)$^+$.

EXAMPLE 3

To a solution of 1,8-napthalimide (198 mg, 1 mmol) in dry DMF (7 mL) was added anhydrous $K_2CO_3$ (552 mg, 4 mmol) and the 1,4-dibromobutane (860 mg, 4 mmol). The reaction mixture was stirred at room temperature for 24 h, until the reaction was monitored by TLC using EtOAc/hexane (2:8) as a solvent system, and then extracted with ethyl acetate and cool water (3×30 mL). The organic phase was dried over $Na_2SO_4$ and evaporated under vacuum to afford the crude product was purified by column chromatography using 10% EtOAc-Hexane as eluent to afford pure compound of white solid 3b (282 mg, 85%)

$^1$H NMR (200 MHz, $CDCl_3$): δ 8.56 (d, 2H), 8.15-8.17 (dd, J=8.30, 1.51 Hz, 2H) 7.74 (t, J=7.5 Hz, 2H) 4.25 (t, 6.79, 2H), 3.45 (t, J=6.7 Hz, 2H), 2.20-2.30 (m, 4H)

MS (EI) 332 [M]$^+$.

To compound 2-(4-bromobutyl)napthalimide 3b (332 mg, 1.2 mmol) in dimethylformamide (8 mL) was added anhydrous $K_2CO_3$ (552 mg, 4 mmol) and the n-Bocpiperazine (186 mg, 1 mmol). The reaction mixture was stirred at room temperature for 24 h, until TLC indicates complete loss of starting material and then potassium carbonate was removed by suction filtration further, evaporated the solvent under vacuum. The crude product was purified by column chromatography using 5% MeOH—$CHCl_3$ as eluent to afford pure compound 6a (327 mg, 75%).

$^1$H NMR (200 MHz, $CDCl_3$): δ 8.46 (d, J=6.0 Hz, 2H), 8.24 (d, J=8.0 Hz, 2H) 7.79 (t, J=7.5 Hz, 2H) 4.17 (t, J=7.5 Hz, 2H), 3.35 (t, J=5.0 Hz, 4H), 2.4-2.5 (m, 2H), 2.3-2.2 (m, 4H), 1.7-1.9 (m, 4H), 1.2-1.5 (m, 9H)

MS (EI) 437 (M)$^+$.

To a solution of Boc-compound 6a (437 mg, 1 mmol) in dry dichloromethane was added trifluoroacetic acid (1 mL) at 0° C. and stirred under nitrogen for 8 h, the reaction mixture was then concentrated in vacuum and it was used directly in next step. To a suspension of this free amine in acetonitrile (10 mL) was added anhydrous $K_2CO_3$ (552 mg, 4 mmol) and the compound 4-(4-bromobutoxy)benzaldehyde (257 mg, 1 mm) and then reaction mixture was stirred at reflux for 24 h, until TLC indicates complete loss of starting material after cooled to room temperature. The potassium carbonate was removed by suction filtration and the solvent was removed under vacuum. The crude product was purified by column chromatography using 10% MeOH—$CHCl_3$ as eluent to afford pure compound 8a (308 mg, 60%).

$^1$H NMR (200 MHz, $CDCl_3$): δ 9.84 (S, 1H), 8.51-8.59 (m, 2H), 8.15-8.19 (dd, J=1.5, 8.30 Hz, 2H), 7.71-7.80 (m, 2H), 7.31 (d, J=4.5 Hz, 2H), 6.95 (d, J=8.3 Hz, 2H), 4.17 (t, J=6.7 Hz, 2H), 4.04 (t, J=6.0 Hz, 2H), 2.31-2.47 (m, 12H), 1.66-1.88 (m, 8H);

ESI M S m/z=514 (M+1)$^+$.

A solution of compound 1a (377 mg, 1.6 mmol) in ethanol (10 mL) was hydrogenated over 10% Pd/C (50 mg) at room temperature for 2 h. After hydrogenation, 4-{4-[4-(4-[2-napthalimido]butyl)piperazino]butoxy}benzaldehyde 8a (543 mg, 1 mmol) and 3 mL of aqueous solution of sodium pyrosulphate (200 mg, 1.5 mmol) in water were added. The reaction mixture was stirred at reflux for 12 h and then cooled to room temperature, until TLC indicates complete loss of starting material. The catalyst was removed by suction filtration and the solvent was removed under vacuum. The crude product was purified by column chromatography using 20% MeOH—$CHCl_3$ as eluent to afford pure compound 9a (385 mg, 55%).

$^1$H NMR (300 MHz $CDCl_3$): δ 8.61 (d, J=7.2 Hz, 2H), 8.27 (d, J=7.9 Hz, 2H), 7.60 (d, J=8.58 Hz, 2H), 7.79 (t, J=7.9 Hz, 2H), 7.53 (d, J=8.7 Hz, 1H), 6.98-7.17 (m, 2H), 6.88 (d, J=7.0 Hz, 2H), 4.41 (t, 2H, J=5.3 Hz), 4.15 (t, 2H, J=6.1 Hz), 3.63-3.72 (m, 4H), 2.50-2.90 (m, 16H), 2.39 (S, 3H), 1.50-1.95 (m, 8H).

ESI M S m/z=701 (M+1)$^+$.

EXAMPLE 4

A solution of compound 1b (356 mg, 1.6 mmol) in ethanol (10 mL) was hydrogenated over 10% Pd/C (50 mg) at room temperature for 2 h. After hydrogenation, 4-{4-[4-(4-[2-napthalimido]butyl)piperazino]butoxy}benzaldehyde 8a (543 mg, 1 mmol) and 3 mL of aqueous solution of sodium pyrosulphate (200 mg, 1.5 mmol) in water were added. The reaction mixture was stirred at reflux for 12 h and then cooled to room temperature, until TLC indicates complete loss of starting material. The catalyst was removed by suction filtration and the solvent was removed under vacuum. The crude product was purified by column chromatography using 20% MeOH—$CHCl_3$ as eluent to afford pure compound 9b (357 mg, 52%).

$^1$H NMR (300 MHz $CDCl_3$): δ 8.60-8.62 (d, J=7.2 Hz, 2H), 8.22-8.32 (d, J=7.9 Hz, 2H), 7.87-8.05 (d, J=8.58 Hz, 2H), 7.73-7.86 (t, J=7.9 Hz, 2H), 7.51-7.58 (d, J=8.7 Hz, 1H), 6.98-7.17 (m, 2H), 6.83-6.92 (d, J=7.0 Hz, 2H), 4.34-4.49 (t, 2H, J=5.3 Hz), 4.09-4.19 (t, 2H, J=6.1 Hz), 3.63-3.72 (m, 4H), 2.50-2.90 (m, 16H), 2.39 (S, 3H), 1.50-1.95 (m, 8H). ESI M S m/z=687 (M+1)$^+$.

EXAMPLE 5

To a solution of 1,8-napthalimide (198 mg, 1 mmol) in dry DMF (7 mL) was added anhydrous $K_2CO_3$ (552 mg, 4 mmol) and the 1,5-dibromopentane (920 mg, 4 mmol). The reaction mixture was stirred at room temperature for 24 h. The reaction was monitored by TLC using EtOAc/hexane (2:8) as a solvent system, and then extracted with ethyl acetate and cool water (3×30 mL). The organic phase was dried over $Na_2SO_4$ and evaporated under vacuum to afford the crude product was purified by column chromatography using 10% EtOAc-Hexane as eluent to afford pure compound of white solide 3c (294 mg, 85%)

$^1$H NMR (200 MHz, $CDCl_3$): δ 8.57 (d, 2H), 8.16-8.19 (dd, J=8.30 Hz, 1.51 Hz, 2H) 7.75 (t, J=7.55, 2H) 4.29 (t, J=6.79, 2H), 3.48 (t, J=6.79, 2H), 2.25-2.35 (q, 2H).

MS (EI) 346 [M]$^+$.

To compound 2-(5-bromopentyl)napthalimide 3c (415 mg, 1.2 mmol) in dimethylformamide (9 mL) was added anhydrous $K_2CO_3$ (552 mg, 4 mmol) and the n-Bocpiperazine (186 mg, 1 mmol). The reaction mixture was stirred at room temperature for 24 h, until TLC indicates complete loss of starting material and then potassium carbonate was removed by suction filtration further evaporated the solvent under vacuum. The crude product was purified by column chromatography using 5% MeOH—$CHCl_3$ as eluent to afford pure compound 6b (315 mg, 70%).

$^1$H NMR (200 MHz, $CDCl_3$): δ 8.45 (d, J=6.0 Hz, 2H), 8.23 (d, J=8.0 Hz, 2H) 7.79 (t, J=7.5 Hz, 2H) 4.15 (t, J=7.5 Hz, 2H), 3.45 (t, J=5.0 Hz, 4H), 2.4-2.5 (m, 2H), 2.3-2.2 (m, 4H), 1.7-1.9 (m, 4H), 1.2-1.5 (m, 9H)

MS (EI) 451 (M)$^+$.

To a solution of Boc-compound 6b (451 mg, 1 mmol) in dry dichloromethane was added trifluoroacetic acid (1 mL) at 0° C. and stirred under nitrogen for 8 h, the reaction mixture was then concentrated in vacuum and it was used directly in next step. To a suspension of this free amine in acetonitrile (10 mL) was added anhydrous $K_2CO_3$ (552 mg, 4 mmol) and the compound 4-(5-bromopentoxy)benzaldehyde (271 mg, 1 mm). The reaction mixture was stirred at reflux for 24 h, until TLC indicates complete loss of starting material and then cooled to room temperature. The potassium carbonate was removed by suction filtration and the solvent was removed under vacuum. The crude product was purified by column chromatography using 10% MeOH—$CHCl_3$ as eluent to afford pure compound 8b (324 mg, 60%).

$^1$H NMR (200 MHz, $CDCl_3$): δ 9.84 (S, 1H), 8.51-8.59 (m, 2H), 8.15-8.19 (dd, J=1.5, 8.30 Hz, 2H), 7.71-7.80 (m, 2H), 7.31 (d, J=4.5 Hz, 2H), 6.95 (d, J=8.3 Hz, 2H), 4.17 (t, J=6.7 Hz, 2H), 4.04 (t, J=6.0 Hz, 2H), 2.31-2.47 (m, 12H), 1.66-1.88 (m, 8H).

ESI M S m/z=542 (M+1)$^+$.

A solution of compound 1b (356 mg, 1.6 mmol) in ethanol (10 mL) was hydrogenated over 10% Pd/C (50 mg) at room temperature for 2 h. After hydrogenation, 4-{5-[4-(5-[2-napthalimido]pentyl)piperazino]pentoxy}benzaldehyde 8b (542 mg, 1 mmol) and 3 mL of aqueous solution of sodium pyrosulphate (200 mg, 1.5 mmol) in water were added. The reaction mixture was stirred at reflux for 12 h and then cooled to room temperature, until TLC indicates complete loss of starting material. The catalyst was removed by suction filtration and the solvent was removed under vacuum. The crude product was purified by column chromatography using 20% MeOH—$CHCl_3$ as eluent to afford pure compound 9c (371 mg, 75%).

$^1$H NMR (300 MHz $CDCl_3$): δ 8.60-8.62 (d, J=7.2 Hz, 2H), 8.22-8.32 (d, J=7.9 Hz, 2H), 7.87-8.05 (d, J=8.58 Hz, 2H), 7.73-7.86 (t, J=7.9 Hz, 2H), 7.51-7.58 (d, J=8.7 Hz, 1H), 6.98-7.17 (m, 2H), 6.83-6.92 (d, J=7.0 Hz, 2H), 4.34-4.49 (t, 2H, J=5.3 Hz), 4.09-4.19 (t, 2H, J=6.1 Hz), 3.63-3.72 (m, 4H), 2.50-2.90 (m, 16H), 2.39 (S, 3H), 1.50-1.95 (m, 8H).

ESI M S m/z=715 (M+1)$^+$.

Biological Activity:

Anticancer activity: In vitro biological activity studies were carried out at the National Cancer Institute (USA).

The compounds 5a-b evaluated for in vitro anticancer activity against sixty human tumour cells derived from nine cancer types (leukemia, non-small-cell lung, colon, CNS, melanoma, ovarian, prostate, and breast cancer) as shown in Table 1. For each compound, dose response curves for each cell line were measured at a minimum of five concentrations at 10 fold dilutions. A protocol of 48 h continuous drug exposure was used and a sulforhodamine B (SRB) protein assay was used to estimate cell viability or growth. The concentration causing 50% cell growth inhibition (GI50), total cell growth inhibition (TGI 0% growth) and 50% cell death (LC50, −50% growth) compared with the control was calculated. The mean graph midpoint values of $\log_{10}$ TGI and $\log_{10}$ LC50 as well as $\log_{10}$ GI50 for 5a and 5b are listed in Table 2. These have exhibited an interesting profile of activity and selectivity for various cell lines. The MG MID of log TGI and log $LC_{50}$ have shown similar pattern to the log $GI_{50}$ MG MID. The other compounds 9a-c evaluated for in vitro one dose anticancer activity against nine human tumor cell panels containing sixty cell lines in percent growth inhibition values are listed in Table 3.

TABLE 1

In vitro anticancer activity of 5a and 5b in selected human cancer cell lines

| Cancer panel/Cell line | $GI_{50}$ (μM) | | | |
|---|---|---|---|---|
| | 5a | 5a$^a$ | 5b | 5b$^a$ |
| Leukemia | | | | |
| K-562 | 0.49 | 1.58 | 2.97 | 3.25 |
| Non-Small Cell Lung Cancer | | | | |
| EKVX | 1.37 | 1.83 | 12.2 | 25.4 |
| NCI-H322M | 1.81 | 1.64 | 0.11 | 40.7 |
| Colon Cancer | | | | |
| HCT-116 | 1.76 | 1.64 | 1.76 | — |
| KM12 | 1.72 | 2.03 | 1.14 | 7.25 |
| SW-620 | 1.70 | 1.83 | 3.19 | 4.49 |
| CNS Cancer | | | | |
| SF-539 | 1.64 | 1.86 | 1.70 | 1.60 |
| SNB-75 | 0.02 | 1.77 | — | — |
| U251 | 1.78 | 1.97 | 1.41 | 1.66 |
| Melanoma | | | | |
| MALME-3M | 7.66 | 2.56 | 0.09 | 3.34 |
| SK-MEL-28 | 1.48 | 1.80 | 1.30 | 1.56 |
| SK-MEL-5 | 1.69 | 1.60 | 1.44 | 1.77 |
| Ovarian Cancer | | | | |
| OVCAR-4 | 1.58 | 1.85 | 1.47 | 2.21 |
| Renal Cancer | | | | |
| 786-0 | 1.53 | 1.74 | 1.21 | 1.37 |
| RXF 393 | — | 10.0 | 0.85 | 0.34 |
| Prostate Cancer | | | | |
| DU 145 | 1.45 | 1.74 | 3.27 | 4.56 |
| Breast Cancer | | | | |
| MCF7 | 1.44 | 1.50 | 3.33 | 2.56 |
| MDA-MB-231/ATCC | 1.51 | 1.41 | 2.51 | 4.25 |
| HS 578T | 2.10 | 2.11 | 0.99 | 4.68 |
| T-47D | 1.54 | 2.66 | 2.20 | 4.32 |
| BT-549 | — | 4.80 | 1.45 | 1.54 |

$^a$Repeat test values

TABLE 2

Log $GI_{50}$, log TGI, and log $LC_{50}$ MG MID of in vitro cytotoxicity data for Compounds 5a and 5b against human tumor cell lines$^a$

| Compd | Log $GI_{50}$ | Log TGI | Log $LC_{50}$ |
|---|---|---|---|
| 5a | −5.34 | −4.80 | −4.20 |
| 5a$^b$ | −5.62 | −5.08 | −4.39 |
| 5b | −5.54 | −4.94 | −4.46 |
| 5b$^b$ | −5.35 | −4.71 | −4.27 |

$^a$$GI_{50}$, drug molar concentration causing 50% cell growth inhibition; TGI, drug concentration causing total cell growth inhibition (0% growth); $LC_{50}$; drug concentration causing 50% cell death (−50%); MG MID, mean graph midpoints, the average sensitivity of all cell lines toward the test agent.
$^b$Repeated test values

TABLE 3

In vitro one dose primary anticancer assay for selected cell lines of compounds 9a-c[a]

| Compd | Cell lines (% GI)[b] | | | | |
| --- | --- | --- | --- | --- | --- |
| | Breast (T-47D) | Ovarian (OVCAR8) | Leukemia (HL-60) | Renal (UO-31) | CNS (SF-295) |
| 9a | 64 | 77 | 84 | 85 | 71 |
| 9b | 50 | 78 | 50 | 68 | 50 |
| 9c | 99 | 89 | 97 | 96 | 84 |

[a]The number reported for the 1-dose assay is growth relative to the no-drug control, and relative to the time zero number of cells. This allows detection of both growth inhibition (values between 0 and 100)
[b]Percent growth inhibition values at $10^{-5}$ Molar concentration

We claim:

1. A naphthalimide-benzimidazole hybrid of formula A

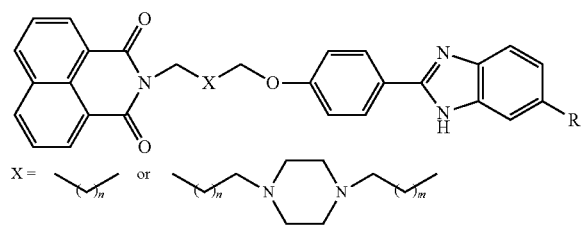

wherein R is n-methylpiperazine or morpholine; n=1-3; m=2-3.

2. The naphthalimide-benzimidazole hybrids as claimed in claim 1, wherein the compounds of formula A are represented by the compounds of formula 5 and 9

Formula 5

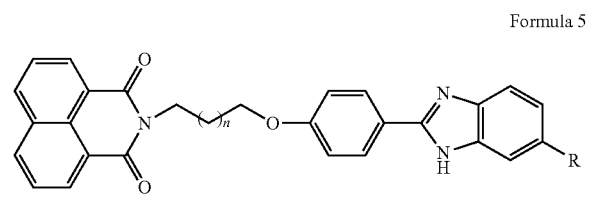

wherein 'n' is 1-2; R=morpholine or n-methylpiperazine

Formula 9

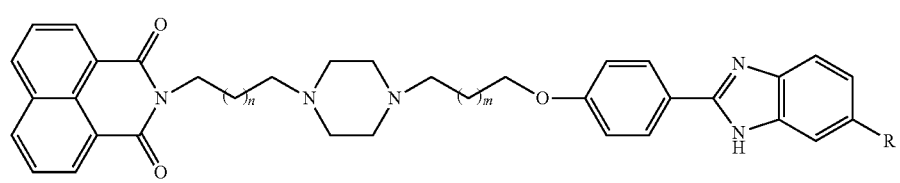

wherein 'n' is 2-3; m is 2-3; R=morpholine or n-methylpiperazine.

3. The naphthalimide-benzimidazole hybrids as claimed in claim 2, wherein the compounds of formula A are:

2-{3-[4-(6-[4-methylpiperazino]2-benzimidazolyl)phenoxy]propyl}napthalimide (5a), 2-{4-[4-(6-morpholino-2-benzimidazolyl)phenoxy]butyl}naphthalimide(5b), 2-{4-[4-(4-[6-[4-methylpiperazino]-2-benzimidazolyl)phenoxy]butyl)piperazino]butyl}napthalimide (9a), 2-{4-[4-(4-[4-(6-morpholino-2-benzimidazolyl)phenoxy]butyl)piperazino]butyl}napthalimide(9b), 2-{5-[4-(5-[4-(6-morpholino-2-benzimidazolyl)phenoxy]pentyl)piperazino]pentyl}napthalimide (9c).

4. The naphthalimide-benzimidazole hybrids as claimed in claim 1 for use as anticancer/antitumour agents.

5. The naphthalimide-benzimidazole hybrids as claimed in claim 1 used as anticancer/antitumour agents against sixty human cancer cell lines derived from nine cancer types selected from the group consisting of leukemia, non-small-cell lung, colon, CNS, melanoma, ovarian, prostate, and breast cancer.

6. The naphthalimide-benzimidazole hybrids as claimed in claim 1, wherein said hybrids exhibit an invitro anticancer/antitymor activity against sixty human cancer cell, lines derived from nine cancer types selected from the group consisting of leukemia, non-small-cell lung, colon, CNS, melanoma, ovarian, prostate, and breast cancer.

7. The naphthalimide-benzimidazole hybrids as claimed in claim 2 for use as anticancer/antitumour agents.

8. The naphthalimide-benzimidazole hybrids as claimed in claim 2 for use as anticancer/antitumour agents against sixty human cancer cell lines derived from nine cancer types selected from the group consisting of leukemia, non-small-cell lung, colon, CNS, melanoma, ovarian, prostate, and breast cancer.

9. The naphthalimide-benzimidazole hybrids as claimed in claim 2 wherein said hybrids exhibit an invitro anticancer/antitymor activity against sixty human cancer cell lines derived from nine cancer types selected from the group consisting of leukemia, non-small-cell lung, colon, CNS, melanoma, ovarian, prostate, and breast cancer.

10. The naphthalimide-benzimidazole hybrids as claimed in claim 3 for use as anticancer/antitumour agents.

11. The naphthalimide-benzimidazole hybrids as claimed in claim 3 for use as anticancer/antitumour agents against sixty human cancer cell lines derived from nine cancer types selected from the group consisting of leukemia, non-small-cell lung, colon, CNS, melanoma, ovarian, prostate, and breast cancer.

12. The naphthalimide-benzimidazole hybrids as claimed in claim 3 wherein said hybrids exhibit an invitro anticancer/antitymor activity against sixty human cancer cell lines derived from nine cancer types selected from the group consisting of leukemia, non-small-cell lung, colon, CNS, melanoma, ovarian, prostate, and breast cancer.

13. A process for the preparation of napthalimide-benzimidazole hybrids of formula A represented by compounds of formula 5 as claimed in claim 2, said process comprising the steps of:

a) reacting 1,8-napthalimide with dibromoalkanes, in the presence of potassium carbonate in DMF and obtaining the compounds 2-(n-bromoalkyl)napthalimide of formula 3a-b,

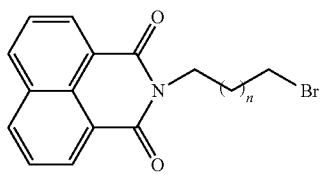

3a-b wherein n=1-2, b) reacting the bromo compounds of formula 3a-b as obtained in step a with 4-hydroxybenzaldehyde in presence of dimethylformamide and $K_2CO_3$, at a temperature of 25-30° C., for a period of 20-30 hrs and obtaining the compound 4-[n-(napthalimide-2-yl)alkoxy]benzaldehyde of formula 4a-b respectively,

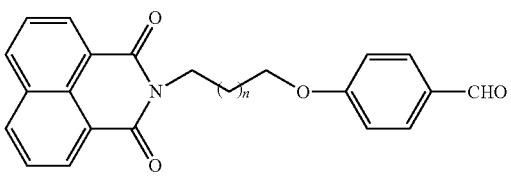

4a-b n = 1-2 c) condensing and oxidizing the aldehyde compounds of formula 4a-b as obtained in step b with diaminobenzene derivatives of formula 4-(4-methylpiperazino)-1,2-benzenediamine or 4-morpholino-1,2-diaminobenzene, in the presence of $Na_2S_2O_5$ and organic solvent selected from methanol and ethanol, under refluxing temperature and obtaining the desired compounds of 2-{3-[4-(6-[4-Methylpiperazino]2-benzimidazolyl)phenoxy]propyl}napthalimide or 2{4-[4-(6-Morpholino-2-benzimidazolyl)phenoxy]buty-1}napthalimide of formula 5a-b respectively

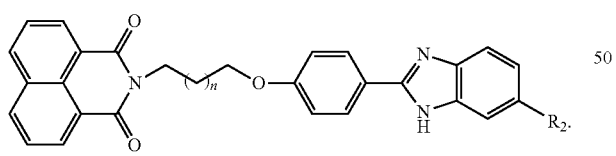

5a, n = 1, $R_2$ = n-methylpiperazine
5b, n = 2, $R_2$ = morpholine

14. A process for the preparation of napthalimide-benzimidazole hybrids of formula A represented by compounds of formula 9 as claimed in claim 2, said process comprising the steps of:

i) reacting 1,8-napthalimide with dibromoalkanes, in the presence of potassium carbonate in DMF and obtaining the compounds 2-(n-bromoalkyl)napthalimide of formula 3b-c,

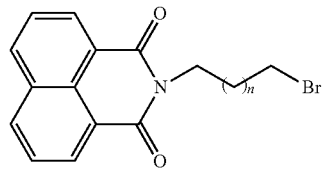

3b-c wherein n=2-3, ii) reacting 2-(n-bromoalkyl)napthalimide of formula 3b-c with n-Bocpiperazine, in the presence of potassium carbonate in DMF and obtaining tert-Butyl4-[n-(2-napthalimido)alkyl]-1-piperazinecarboxylate of formula 6a-b respectively,

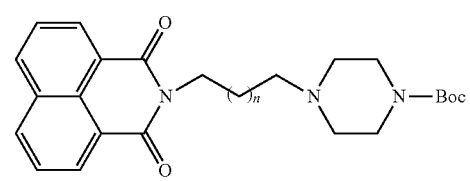

6a-b n = 2-3 iii) deprotecting the compounds of formula 6a-b as obtained in step(ii) using trifluoro acetic acid, in the presence of dichloromethane at about 0° C., for a period of 10-20 hrs and obtaining the compound 4-[n-(2-napthalimido)alkyl]-1-piperazine of formula 7a-b respectively,

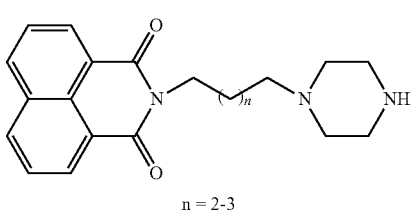

7a-b n = 2-3 iv) reacting the free amine compounds of formula 7a-b as obtained in step (iii) with bromo alkoxy benzaldehydes, in the presence of acetonitrile/$K_2CO_3$, at refluxing temperature, for a period of 20-25 hrs and obtaining the compound of 4-{n-[4-(n-[2-Napthalimido]alkyl)piperazino]alkoxy}benzaldehyde of formula 8a-b respectively,

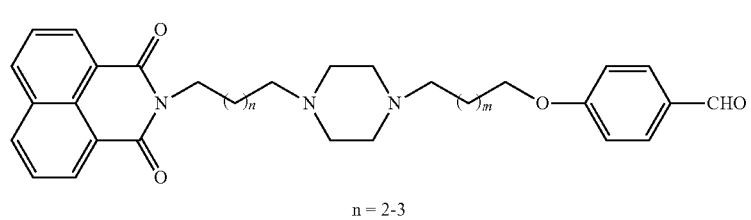

v) condensing and oxidizing said aldehyde compounds of formula 8a-b as obtained in step (iv) with diaminobenzene derivatives of formula 2a-b

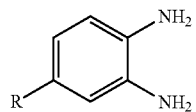

wherein R=n-methylpiperazine or morpholine, $Na_2S_2O_5$ and organic solvent selected from methanol and ethanol, under refluxing temperature and obtaining the desired compounds of novel napthalimide-benzimidazole hybrids of formula 9a-c respectively

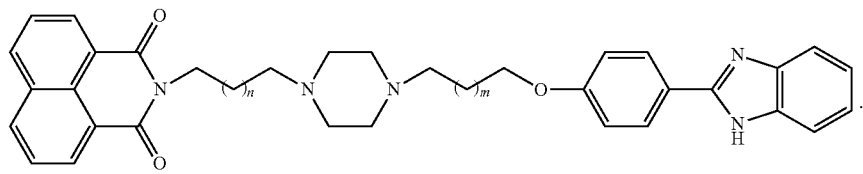

9a, n = 2, m = 2, $R_1$ = n-methylpiperazine
9b, n = 2, m = 2, $R_1$ = morpholine
9c, n = 3, m = 3, $R_1$ = morpholine

\* \* \* \* \*